US010129846B2

(12) United States Patent
Hayami et al.

(10) Patent No.: US 10,129,846 B2
(45) Date of Patent: Nov. 13, 2018

(54) INFORMATION ANALYSIS SYSTEM FOR TRANSMITTING INFORMATION THAT REQUIRES TIMING SYNCHRONIZATION

(71) Applicant: JVC KENWOOD Corporation, Yokohama-shi, Kanagawa (JP)

(72) Inventors: Atsushi Hayami, Yokohama (JP); Hisashi Terada, Yokohama (JP)

(73) Assignee: JVC KENWOOD Corporation, Tokyo (JP)

( * ) Notice: Subject to any disclaimer, the term of this patent is extended or adjusted under 35 U.S.C. 154(b) by 226 days.

(21) Appl. No.: 15/152,341

(22) Filed: May 11, 2016

(65) Prior Publication Data

US 2016/0255600 A1 Sep. 1, 2016

Related U.S. Application Data

(63) Continuation of application No. PCT/JP2014/076013, filed on Sep. 30, 2014.

(30) Foreign Application Priority Data

Nov. 13, 2013 (JP) .................. 2013-235273
Nov. 13, 2013 (JP) .................. 2013-235274
Nov. 13, 2013 (JP) .................. 2013-235275

(51) Int. Cl.
*H04J 3/06* (2006.01)
*H04W 56/00* (2009.01)
(Continued)

(52) U.S. Cl.
CPC ......... *H04W 56/004* (2013.01); *A61B 5/0022* (2013.01); *A61B 5/0432* (2013.01);
(Continued)

(58) Field of Classification Search
CPC ............ H04W 56/004; H04W 56/0055; H04L 7/0091; A61B 5/0022; A61B 5/0432;
(Continued)

(56) References Cited

U.S. PATENT DOCUMENTS

| 5,690,111 | A | * | 11/1997 | Tsujino | ................ A61B 5/0456 600/440 |
| 5,802,211 | A | * | 9/1998 | King | ....................... G10L 19/04 348/699 |
| 8,861,550 | B2 | * | 10/2014 | Park | ................... H04N 13/0062 370/472 |
| 2003/0037158 | A1 | * | 2/2003 | Yano | ...................... H04L 29/06 709/232 |

(Continued)

FOREIGN PATENT DOCUMENTS

| JP | H05-150032 A | 6/1993 |
| JP | 2011-212167 A | 10/2011 |
| WO | 2012-008264 A1 | 1/2012 |

*Primary Examiner* — Kevin D Mew

(74) *Attorney, Agent, or Firm* — Brundidge & Stanger, P.C.

(57) ABSTRACT

An input unit inputs detected information that has been acquired by a sensor. By inserting time information into the detected information that has been input, a multiplexer generates an information sequence in which the detected information and the time information are multiplexed in a time-dividing manner. A transmission unit transmits the information sequence. The time information in the multiplexer is used to synchronize timing between detected information included in an information sequence transmitted from another transmitter and the detected information in the multiplexer.

5 Claims, 17 Drawing Sheets

(51) Int. Cl.
*A61B 5/00* (2006.01)
*A61B 5/0432* (2006.01)
*A61B 5/0452* (2006.01)
*H04L 7/00* (2006.01)
*G06F 19/00* (2018.01)
*G16H 40/67* (2018.01)

(52) U.S. Cl.
CPC .......... *A61B 5/0452* (2013.01); *A61B 5/6805* (2013.01); *A61B 5/7282* (2013.01); *A61B 5/746* (2013.01); *G06F 19/00* (2013.01); *G16H 40/67* (2018.01); *H04L 7/0091* (2013.01); *H04W 56/0055* (2013.01); *A61B 2505/01* (2013.01); *H04J 3/0638* (2013.01)

(58) Field of Classification Search
CPC ... A61B 5/0452; A61B 5/6805; A61B 5/7282; A61B 5/746; A61B 2505/01
See application file for complete search history.

(56) References Cited

U.S. PATENT DOCUMENTS

| | | | |
|---|---|---|---|
| 2003/0043915 A1* | 3/2003 | Costa | H04N 21/23418 375/240.24 |
| 2003/0152145 A1* | 8/2003 | Kawakita | H04N 5/77 375/240.12 |
| 2003/0169810 A1* | 9/2003 | Costa | H04N 21/2343 375/240.03 |
| 2004/0133379 A1* | 7/2004 | Kobayashi | G06F 3/011 702/127 |
| 2004/0143849 A1* | 7/2004 | Costa | H04N 7/17336 725/95 |
| 2004/0143850 A1* | 7/2004 | Costa | H04N 7/17318 725/115 |
| 2007/0082672 A1* | 4/2007 | Fujioka | H04B 7/26 455/436 |
| 2008/0247336 A1* | 10/2008 | Sugitani | H04B 7/2643 370/280 |
| 2014/0016568 A1* | 1/2014 | Koskela | H04W 52/0206 370/329 |

* cited by examiner

INFORMATION ANALYSIS SYSTEM FOR TRANSMITTING INFORMATION THAT REQUIRES TIMING SYNCHRONIZATION

CROSS-REFERENCE TO RELATED APPLICATION

This application is based upon and claims the benefit of priority from the prior Japanese Patent Application No. 2013-235273, filed on Nov. 13, 2013, Japanese Patent Application No. 2013-235274, filed on Nov. 13, 2013, and Japanese Patent Application No. 2013-235275, filed on Nov. 13, 2013, the entire contents of which are incorporated herein by reference.

BACKGROUND

1. Field

The present invention relates to transmission technology, and particularly to information analysis systems for transmitting information that requires timing synchronization.

2. Description of the Related Art

At scenes of disaster, various types of measuring instruments for measuring biological information are used. Biological information that has been measured is transmitted to biological information monitoring devices via a communication network. Operation of the biological information monitoring devices performed by observers facilitates relief activities (for example, Patent Document 1).

Patent Document 1: Japanese Patent Application Publication No. 2011-212167

Firefighters, etc., who are engaged in relief activities at scenes of disaster are at risk of losing their lives in the line of duty. Particularly in the United States, the main cause for a loss of life in the line of duty is a heart attack at scenes of disaster, followed by suffocation due to smoke or toxic gas, or external injuries caused by dangerous operations associated with rescue or firefighting. In order to prevent this, detection of biological information and circumstances of the firefighters is desired. For example, if abnormality is detected when the firefighters' cardioelectricity, heart rate, etc., are monitored as biological information, some kind of treatment should be provided accurately and promptly. In order to find abnormality through the detection of biological information, multiple electrocardiographic monitors are worn at multiple sites of the body in the case of an electrocardiogram, and a diagnosis is made based on changes in respective waveforms in the same time period. Abnormality is also detected based on multiple different pieces of biological information such as an electrocardiogram, a pulse wave, etc., in the same time period.

By putting sensors for detecting biological information on firefighters and using wireless technology and Internet technology, a diagnosis can be made at remote locations. If multiple sensors are used to increase the accuracy of abnormality detection, timing synchronization between signals of the sensors is necessary in that case. In the case of transmitting the signals of the sensors with use of the wireless technology and the Internet technology, a time difference is generated between the signals depending on a traffic condition even when the signals are transmitted at the same time. As a result, even pieces of biological information that are received at the same time by the receiver, the pieces of biological information are not always those acquired at the same timing. Therefore, it is difficult to make a diagnosis using multiple different pieces of biological information such as an electrocardiogram, a pulse wave, etc., in the same time frame.

SUMMARY

An information analysis system according to one aspect of the present embodiment includes: a plurality of transmitters; and a receiver. Each of the plurality of transmitters includes: an input unit that inputs detected information; an information sequence generation unit that generates an information sequence including the detected information that has been input to the input unit and time information that corresponds to the detected information; and a transmission unit that transmits the information sequence generated by the information sequence generation unit. The receiver includes: a reception unit that receives respective information sequences from the plurality of transmitters; and a processing unit that analyzes, based on time information included in the plurality of information sequences received by the reception unit, detected information included in the plurality of information sequences. The transmitters include an imaging device. The detected information is image data captured by the imaging device.

Optional combinations of the aforementioned constituting elements and implementations of embodiments in the form of methods, apparatuses, systems, recording mediums, and computer programs may also be practiced as additional modes of the embodiments.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION

The invention will now be described by reference to the preferred embodiments. This does not intend to limit the scope of the present invention, but to exemplify the invention.

First Exemplary Embodiment

A brief description of the present invention will be given first before a specific description thereof is given. An exemplary embodiment relates to an information analysis system that includes a sensor and a transmitter worn by a user such as a firefighter and a receiver that is connected to these sensor and transmitter via a network. The sensor and the transmitter are connected on a one-to-one basis. In order to acquire a plurality of types of biological information pieces from a single user, a plurality of types of sensors are worn by the single user. Therefore, a plurality of transmitters are also worn by the single user. Upon receiving respective pieces of detected information from the plurality of sensors via the plurality of transmitters and the network, the receiver detects abnormality occurring in the user by analyzing those pieces of detected information. Since the network is formed by a wireless circuit, the Internet, etc., there is variation in transmission delay depending on a traffic condition. When there is variation in transmission delay, a plurality of pieces of detected information acquired at the same timing by different sensors are received by the receiver at different timing. With such a plurality of pieces of detected information, the analysis for detecting abnormality in the user cannot be accurately performed.

To cope with this, a transmitter according to a first exemplary embodiment is provided with a means for acquiring time information and acquires time information by receiving a signal from, e.g., a global positioning system (GPS) satellite. The time information may be acquired by receiving a signal of a standard wave. The transmitter multiplexes detected information and time information in a time-dividing manner so that time information is inserted between pieces of detected information of a sensor. The transmitter transmits information that has been multiplexed in a time-dividing manner (hereinafter, referred to as "information sequence"). The receiver receives an information sequence from each of the plurality of transmitters. The receiver performs timing synchronization on detected information included in each of a plurality of information sequences by using time information included in the information sequences. As a result, analysis based on a plurality of pieces of detected information on which timing synchronization has been performed is possible in the receiver.

Figure 1:
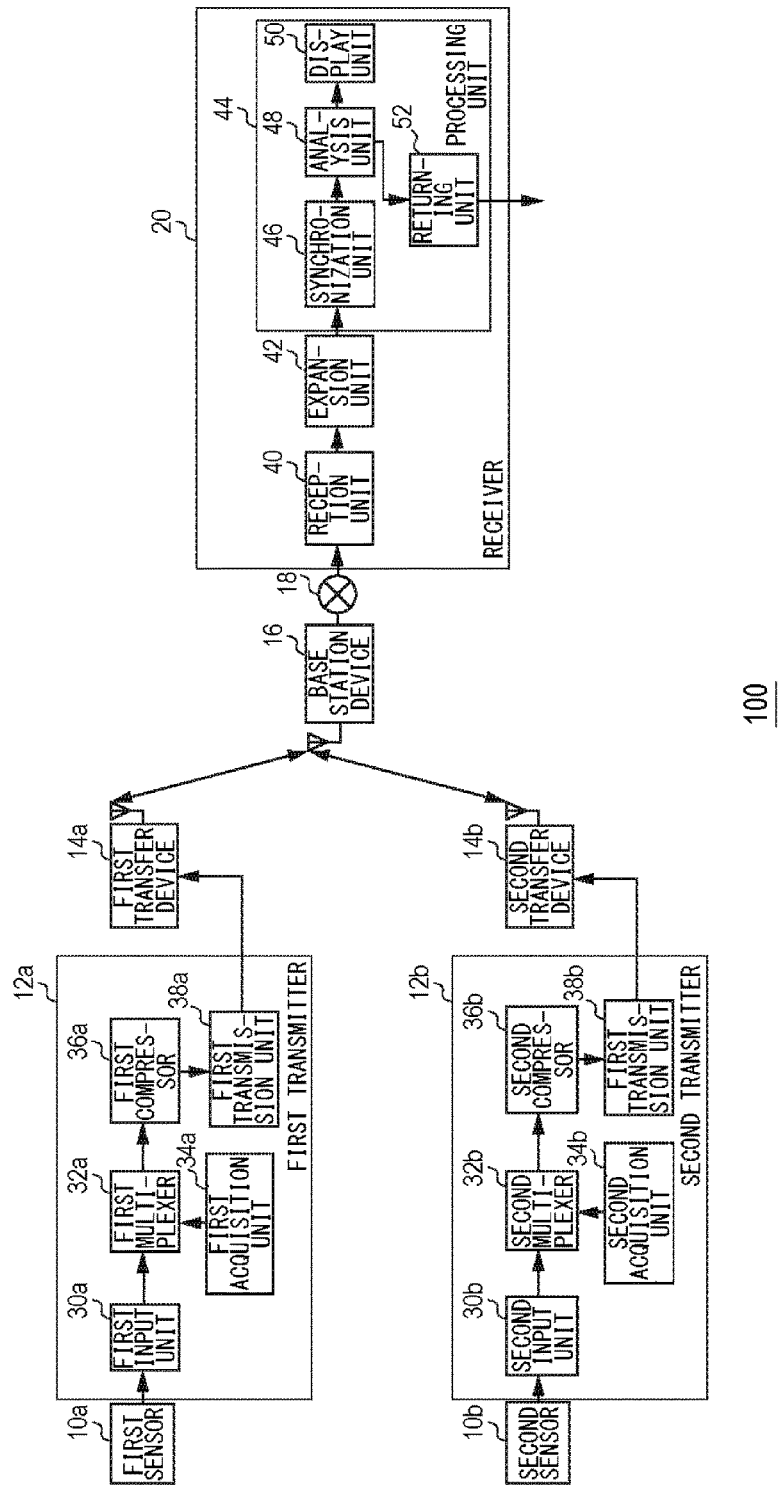
FIG. 1 is a diagram illustrating the configuration of an information analysis system according to a first exemplary embodiment.

FIG. 1 illustrates the configuration of an information analysis system 100 according to the first exemplary embodiment. The information analysis system 100 includes: a first sensor 10a and a second sensor 10b, which are generically referred to as sensors 10; a first transmitter 12a and a second transmitter 12b, which are generically referred to as transmitters 12; a first transfer device 14a and a second transfer device 14b, which are generically referred to as transfer devices 14; a base station device 16; a network 18; and a receiver 20. The first transmitter 12a includes: a first input unit 30a; a first multiplexer 32a; a first acquisition unit 34a; a first compressor 36a; and a first transmission unit 38a. The second transmitter 12b includes: a second input unit 30b; a second multiplexer 32b; a second acquisition unit 34b; a second compressor 36b; and a second transmission unit 38b. The first input unit 30a and the second input unit 30b are generically referred to as input units 30. The first multiplexer 32a and the second multiplexer 32b are generically referred to as multiplexers 32. The first acquisition unit 34a and the second acquisition unit 34b are generically referred to as acquisition units 34. The first compressor 36a and the second compressor 36b are generically referred to as compressors 36. The first transmission unit 38a and the second transmission unit 38b are generically referred to as transmission units 38. The receiver 20 includes: a reception unit 40; an expansion unit 42; and a processing unit 44. The processing unit 44 includes: a synchronization unit 46; an analysis unit 48; a display unit 50; and a returning unit 52.

A sensor 10 is wearable by a person and measures biological information such as cardioelectricity, myoelectricity, pulse wave, heart rate, body temperature, etc., of the person wearing the sensor 10. A single sensor 10 measures a single type of biological information, e.g., pulse wave. Biological information that has been detected (hereinafter, referred to as "detected information") is output in the form of a digital value. An input unit 30 is connected to a sensor 10 on a one-to-one basis and inputs detected information that has been acquired by the sensor 10.

Figure 2:
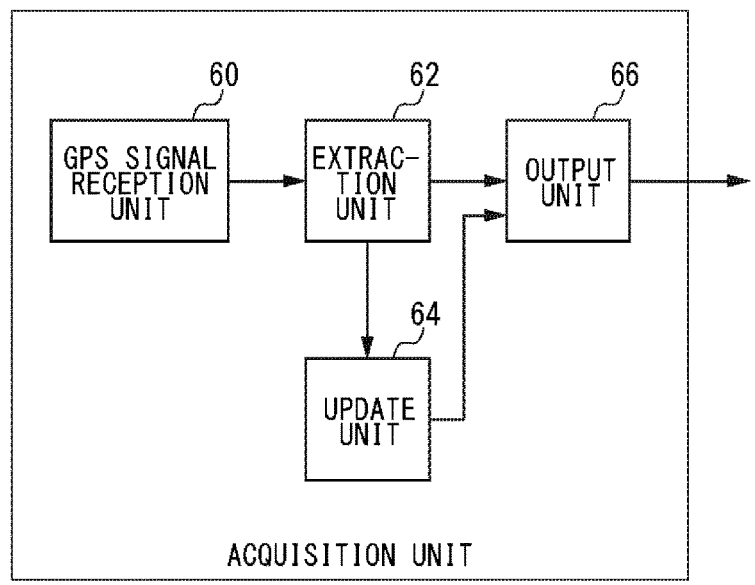
FIG. 2 is a diagram illustrating the configuration of an acquisition unit shown in FIG. 1.

An acquisition unit 34 acquires time information generated based on a signal from a global positioning system (GPS) satellite. FIG. 2 illustrates the configuration of the acquisition unit 34. A multiplexer 32 includes: a GPS signal reception unit 60; an extraction unit 62; an update unit 64; and an output unit 66. The GPS signal reception unit 60 receives a signal from a GPS satellite, and the extraction unit 62 acquires time information from the signal from the GPS satellite. Publicly-known techniques may be used for these operations, and the explanation thereof is thus omitted.

When the time information is not acquired in the GPS signal reception unit 60 and the extraction unit 62, i.e., when the acquisition of the time information is failed, the update unit 64 generates the time information by updating time information that has already been acquired. When the time information is acquired in the extraction unit 62, the output unit 66 outputs the time information acquired in the extraction unit 62 to the multiplexer 32. On the other hand, when the acquisition of the time information is failed in the extraction unit 62, the output unit 66 outputs the time information generated by the update unit 64 to the multiplexer 32. FIG. 1 is referred back.

Figure 3:
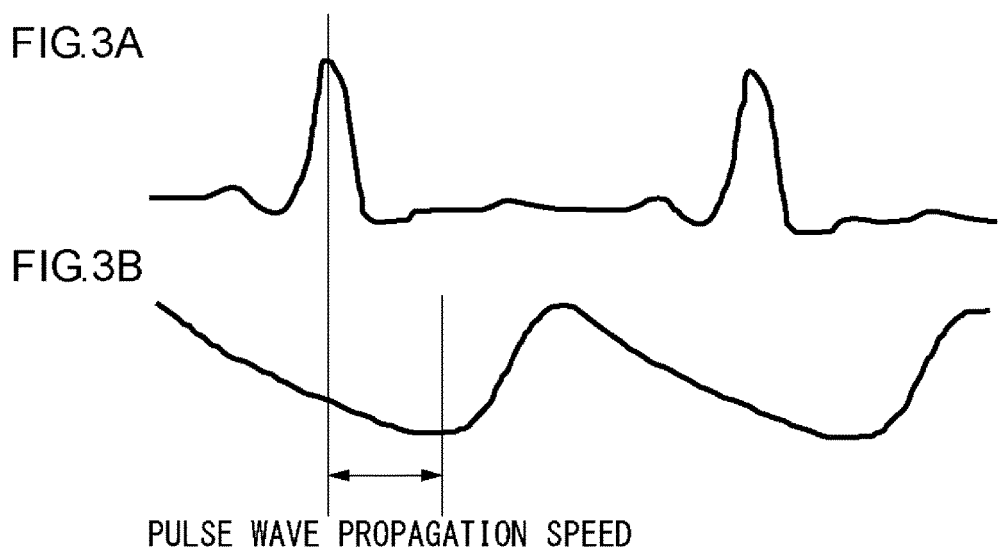
FIGS. 3A-3B are diagrams showing biological information detected by a sensor shown in FIG. 1.

By inserting time information into the detected information that has been input to the input unit 30, the multiplexer 32 generates an information sequence in which the detected information and the time information are multiplexed in a time-dividing manner. An example of the detected information will be given, and the reason why the time information is necessary will be explained. FIGS. 3A-3B show biological information detected by a sensor 10. FIG. 3A shows an electrocardiogram, and FIG. 3B shows a pulse wave. These are pieces of biological information acquired by different sensors 10. The difference in time between a peak point of the electrocardiogram and a minimum value point of the pulse wave is referred to as a pulse wave propagation speed, and the amount of this time becomes, for example, an index that indicates arteriosclerosis or the like, which is one of the causes for a heart attack. As described previously, when the detected information is transmitted to the receiver 20, a time difference is caused between the electrocardiogram and the pulse wave due to the base station device 16 and the network 18 that exist along the way, and information such as a pulse wave propagation speed cannot be obtained accurately. FIG. 1 is referred back.

Figure 4:
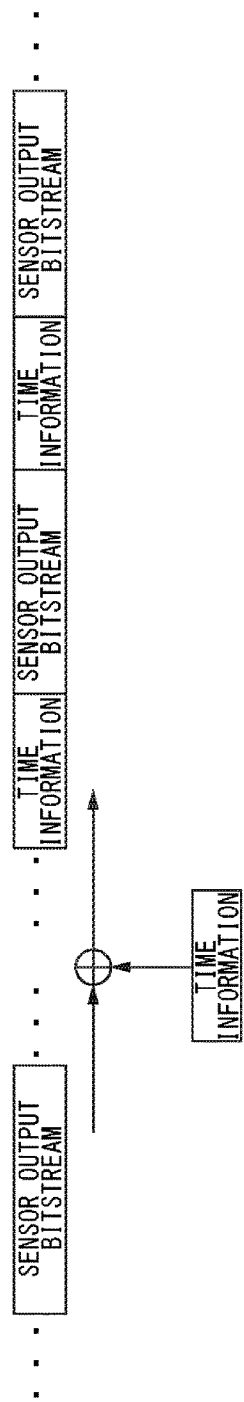
FIG. 4 is a diagram illustrating processing details performed by a multiplexer shown in FIG. 1.

FIG. 4 illustrates processing details performed by the multiplexer 32. Detected information from the input unit 30 is shown as "sensor output bitstream." As shown in the figure, time information is inserted between sensor output bitstreams at predetermined intervals. Detected information, which is a single "sensor output bitstream," and a single piece of time information together form a single combination. Such time information in the multiplexer 32 is used to synchronize timing between detected information included in an information sequence transmitted from another transmitter 12 and detected information in the multiplexer 32. FIG. 1 is referred back.

A compressor 36 compresses an information sequence generated by the multiplexer 32 and outputs a compressed information sequence to a transmission unit 38. Such compression is performed such that the information sequence can be reproduced in the expansion unit 42, which is described later. This compression method may be lossless compression or may be lossy conversion that allows for diagnosis and time synchronization. The compression is performed to lower the transmission speed and facilitates the transmission. In this case, the compression is performed after time division multiplexing. Alternatively, time division multiplexing may be performed after the compression. Further, only an information sequence may be compressed, and time information may not be compressed.

The transmission unit 38 transmits a signal in which the information sequence from the compressor 36 is included. The transmission unit 38 transmits the signal by weak radio waves that are adaptable to a predetermined wireless personal area network (PAN), a wireless body area network (BAN), etc. Wireless PAN and wireless BAN are publicly-known techniques. Thus, the explanation thereof is omitted. A transfer device 14 receives the signal from the transmission unit 38. The transfer device 14 transmits the signal that has been received to the base station device 16. The transfer device 14 performs communication through a PAN with the transmitter 12 and executes a mobile telephone communication system, a wireless metropolitan area network (MAN), and a wireless local area network (LAN) with the base station device 16. In other words, the transfer device 14 performs wireless communication with high transmission power with the latter compared to with the former. The transmission unit 38 may be adaptable to a mobile telephone communication system, a metropolitan area network (MAN), and a wireless local area network (LAN) instead of a PAN or BAN. The transfer device 14 is omitted in that case.

The base station device 16 connects to a plurality of transfer devices 14 at one end thereof and connects to the network 18 at the other end thereof. The base station device 16 transmits a signal received from a transfer device 14 to the network 18. The base station device 16 adds a predetermined address of a transmission source, a transmission destination, or the like to the signal that has been received and performs protocol conversion on the signal. The base station device 16 then transmits the signal to the network 18. Since the base station device 16 relays a signal from each of the plurality of transfer devices 14, the base station device 16 is considered to relay a plurality of types of detected information.

The reception unit 40 receives a signal from the base station device 16 via the network 18. In other words, the reception unit 40 receives an information sequence from each of the plurality of transmitters 12. The reception unit 40 temporarily stores the information sequence that has been received. As described previously, in an information sequence, by the insertion of time information into detected information acquired by a sensor 10, the detected information and the time information are multiplexed in a time-dividing manner. The receiver 20 is assumed to be set in a control room for firefighters, etc. The expansion unit 42 expands a plurality of information sequences received by the reception unit 40 and outputs the plurality of information sequences that have been expanded to the processing unit 44. Expansion processing performed by the expansion unit 42 corresponds to reverse processing of compression processing performed by the compressor 36.

The synchronization unit 46 receives the plurality of information sequences from the expansion unit 42. The synchronization unit 46 extracts time information included in each of the plurality of information sequences that have been received. The synchronization unit 46 adjusts the timing of detected information so as to match the timing of the time information included in each of the plurality of information sequences. As a result, timing is synchronized among respective pieces of detected information included in the plurality of information sequences. As described, the processing unit 44 processes the plurality of information sequences received by the reception unit. When time division multiplexing is performed after the compression in the transmitters 12, the order of the processing in the expansion unit 42 and the processing in the synchronization unit 46 may be reversed.

The analysis unit 48 analyzes the plurality of pieces of detected information whose timing has been synchronized by the synchronization unit 46. Publicly-known techniques may be used for the analysis, and the explanation thereof is thus omitted. Abnormality is detected by the analysis. As the result of the analysis in the analysis unit 48, the display unit 50 displays biological information as shown in FIGS. 3A-3B. Based on the biological information displayed on the display unit 50, a doctor or the like may make a diagnosis. As a result, a judgment is made by a doctor regarding abnormal states. When abnormality is detected in the analysis unit 48 or when abnormality is detected by the diagnosis from the doctor, the returning unit 52 returns the detection result to a predetermined return destination. The return destination may be the user himself/herself, a firefighting command vehicle, a family member, or a nearby hospital.

The configuration is implemented in hardware by any CPU of a computer, memory or other LSI's, and in software by a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

According to the present exemplary embodiment, since time information is multiplexed in a time-dividing manner on detected information, timing can be synchronized among pieces of the detected information. Further, since the timing is synchronized among the pieces of the detected information, analysis can be performed with use of a relative relationship between pieces of biological information. Since analysis where the relative relationship between the pieces of biological information is used is performed, the accuracy of detecting an abnormal state can be improved. Also, since new time information is generated by the updating of already-acquired time information in the case of a failure in the acquisition of time information based on a signal from a GPS satellite, highly accurate time information can be used. Since biological information is monitored with regard to the physical conditions of a firefighter being engaged in activities at scenes of disaster, abnormal states can be detected early. Further, since abnormal states are detected early, proper treatment can be received before a serious situation develops such as a loss of life due to a heart attack. Also, since an abnormal state is returned, treatment that is based on a diagnosis result and a coping method that are returned is promptly provided to the user wearing a corresponding sensor at the return destination. Thus, a loss of life due to a heart attack or the like can be prevented from occurring. If GPS position information is also transmitted, the position where the user wearing the sensor exists can be found. Thus, the user can be quickly rescued based on the position information when rescue is necessary.

Second Exemplary Embodiment

A second exemplary embodiment will be described next. As in the case of the first exemplary embodiment, the second exemplary embodiment relates to an information analysis system that includes a sensor and a transmitter worn by a user such as a firefighter and a receiver that is connected to these sensor and transmitter via a network. As in the case of the first exemplary embodiment, the transmitter compresses time information and detected information, and the receiver performs expansion. If processing delay in the receiver becomes large due to an increase in the traffic volume of a signal received by the receiver, the latest biological information is not processed. If the biological information is not new, delay also occurs in the detection of abnormality. Even under such a situation, an information analysis system according to the second exemplary embodiment performs subsequent processing in order to update biological information to be processed in the receiver.

The transmitter generates an information sequence by also multiplexing a change tag in a time-dividing manner when multiplexing the time information and the detected information in a time-dividing manner. The change tag represents information that shows the magnitude of a change in the value of the detected information. For example, the change tag is set to "1" if the magnitude of the change is large, and the change tag is set to "0" if the magnitude of the change is small. A processing period of the expansion processing in the receiver tends to be long compared to a period of another processing. When the processing delay is large, the receiver checks the change tag. If the change tag is "0," the receiver omits expansion processing of the corresponding time information and detected information. On the other hand, if the change tag is "1," the receiver performs the expansion processing of the corresponding time information and detected information. Since the expansion processing is omitted when the magnitude of a change in the biological information is small, processing delay is reduced.

Figure 5:
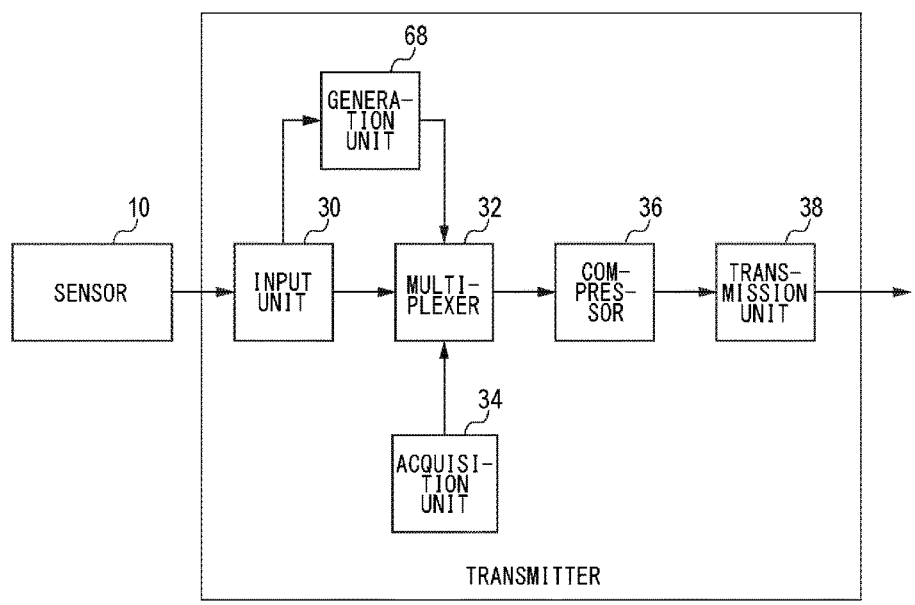
FIG. 5 is a diagram illustrating the configuration of a transmitter according to a second exemplary embodiment.

FIG. 5 illustrates the configuration of a transmitter 12 according to the second exemplary embodiment. The transmitter 12 includes an input unit 30, a multiplexer 32, an acquisition unit 34, a compressor 36, a transmission unit 38, and a generation unit 68. An explanation will be given mainly regarding the difference from the transmitter 12 shown in FIG. 1.

Figure 6:
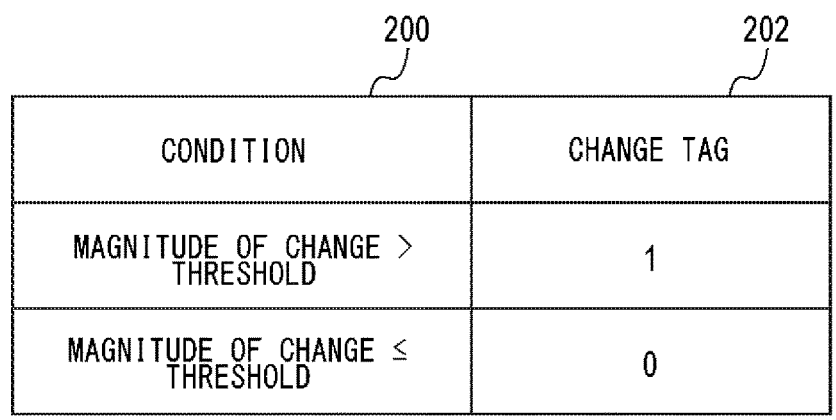
FIG. 6 is a diagram illustrating a data structure of a table stored in a generation unit shown in FIG. 5.

The generation unit 68 derives the magnitude of a change in the value of detected information that is input to the input unit 30. The magnitude of the change is derived, for example, as variance and standard deviation in the value of the detected information included in the previously-described single combination. The magnitude of the change may be derived as a difference between the maximum value and the minimum value in the value of the detected information included in the single combination. The generation unit 68 generates a change tag based on the magnitude of the change that is derived. A table is used for the generation of the change tag. FIG. 6 illustrates a data structure of a table stored in the generation unit 68. As illustrated in the figure, a condition column 200 and a change tag column 202 are included. If the magnitude of the change is larger than a threshold, the generation unit 68 sets the change tag to "1." If the magnitude of the change is the threshold or less, the generation unit 68 sets the change tag to "0." FIG. 5 is referred back. Such a change tag shows the magnitude of a change in the value of the detected information. The generation unit 68 outputs the change tag to the multiplexer 32.

Figure 7:
FIG. 7 is a diagram illustrating processing details performed by a multiplexer shown in FIG. 5.

The multiplexer 32 inputs the change tag from the generation unit 68. The multiplexer 32 also multiplexes, in a time-dividing manner, the change tag generated by the generation unit 68 in addition to detected information and time information when generating an information sequence. FIG. 7 illustrates processing details performed by the multiplexer 32. As shown in the figure, the combination of a change tag, time information, and a sensor output bitstream is arranged in succession. As previously described, the change tag shows the magnitude of a change in the sensor output bitstream in the combination. FIG. 5 is referred back. The compressor 36 performs compression as in the case of the first exemplary embodiment. However, in the information sequence, at least change tags are not subject to compression.

The configuration of a receiver 20 in the second exemplary embodiment is similar in type to that of FIG. 1. In addition to detected information and time information, change tags are also multiplexed in a time-dividing manner in each of a plurality of information sequences received by a reception unit 40. As described previously, in the information sequences, at least change tags are not subject to compression.

An expansion unit 42 measures processing delay in expansion processing. The measurement of the processing delay is performed, for example, by measuring the period from the entry of an information sequence to the expansion unit 42 until the end of expansion processing performed on the information sequence. The period may be until the start of the expansion processing instead of until the end of the expansion processing. The expansion unit 42 expands the information sequence if the processing delay is a threshold or less. Since change tags are excluded from being compressed, change tags are also excluded from the application of expansion. On the other hand, if the processing delay is larger than the threshold, the expansion unit 42 checks the value of a change tag. If the change tag is "1," the expansion unit 42 expands corresponding detected information. If the change tag is "0," the expansion unit 42 skips the expansion of the corresponding detected information. In other words, the expansion unit 42 determines whether or not to perform expansion according to the value of the change tag.

Figure 8:
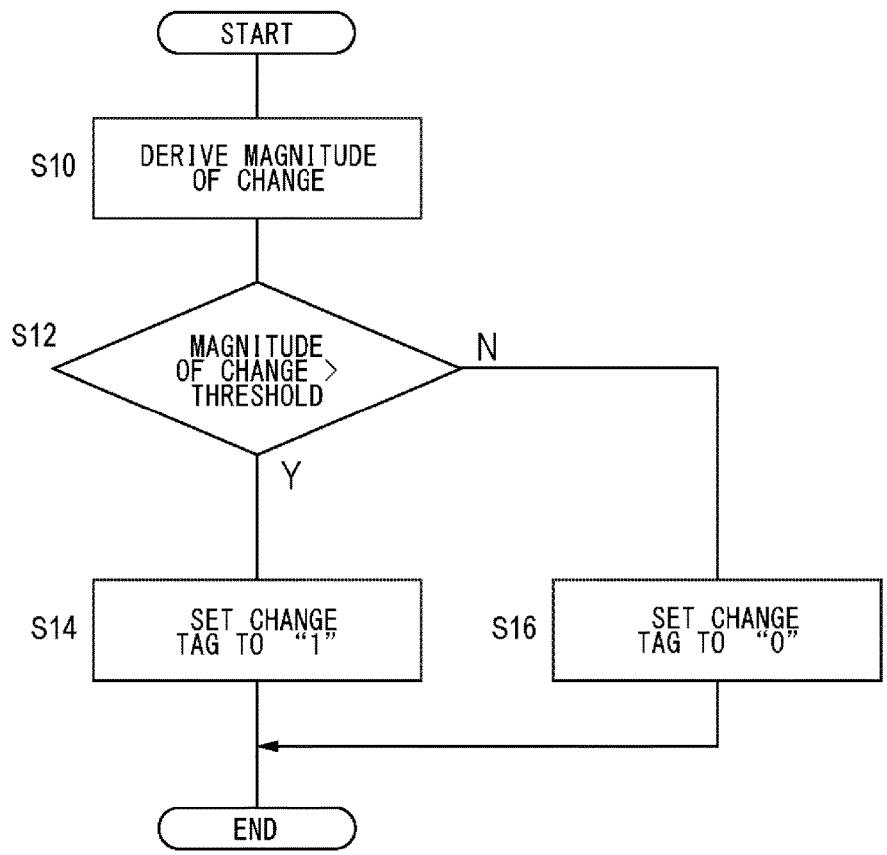
FIG. 8 is a flowchart illustrating a procedure of setting a change tag by a transmitter shown in FIG. 5.

An explanation will be given of the operation of an information analysis system 100 having the above-stated configuration. FIG. 8 is a flowchart illustrating a procedure of setting a change tag by the transmitter 12. The generation unit 68 derives the magnitude of a change (S10). If the magnitude of the change is larger than the threshold (Y in S12), the generation unit 68 sets the change tag to "1" (S14). On the other hand, if the magnitude of the change is not larger than the threshold (N in S12), the generation unit 68 sets the change tag to "0" (S16).

Figure 9:
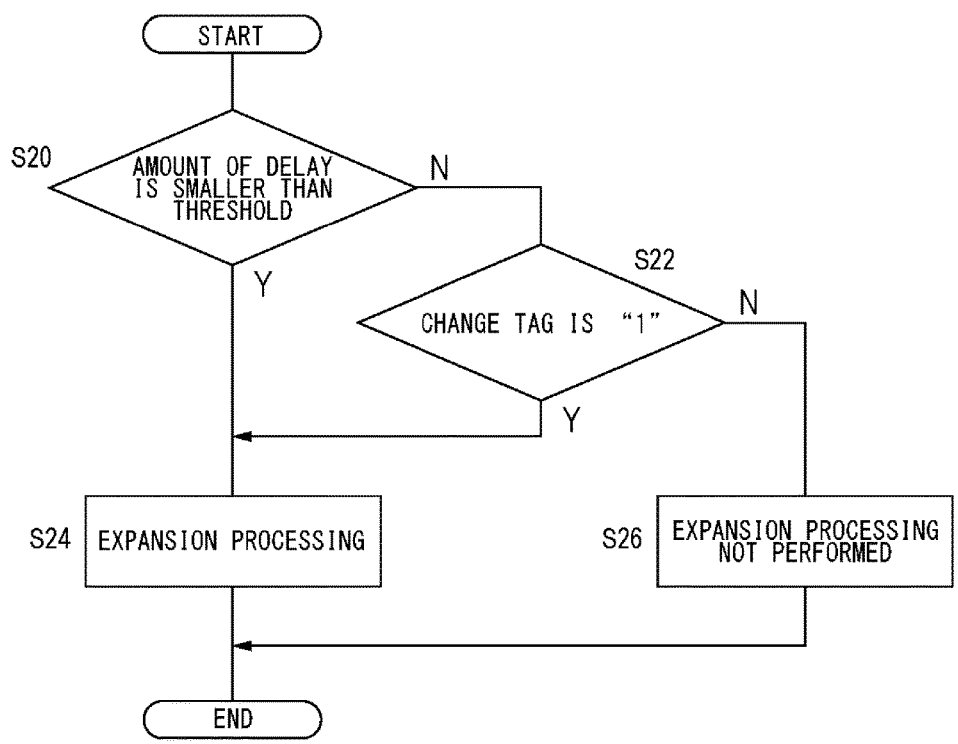
FIG. 9 is a flowchart illustrating an expansion procedure performed by a receiver according to the second exemplary embodiment.

FIG. 9 is a flowchart illustrating an expansion procedure performed by the receiver 20 according to the second exemplary embodiment. If the amount of delay is smaller than a threshold (Y in S20), the expansion unit 42 performs expansion processing (S24). If the amount of delay is not smaller than the threshold (N in S20), the expansion unit 42 performs expansion processing (S24) as long as the change tag is "1" (Y in S22). If the change tag is not "1" (N in S22), the expansion unit 42 does not perform expansion processing (S26).

According to the exemplary embodiment, information that can be quickly acquired can be transmitted since change tags are transmitted without being compressed. Also, since change tags are not compressed, processing delay caused until the details of the change tags are checked can be shortened. Since the processing delay caused until the details of the change tags are checked is shortened, the period spent until the checking can be shortened. Also, since time information and detected information are checked when a change is shown to be large in change tags, only necessary information can be acquired in a short period of time.

Third Exemplary Embodiment

A third exemplary embodiment will be described next. As in the case of the previous exemplary embodiments, the third exemplary embodiment relates to an information analysis system that includes a sensor and a transmitter worn by a user such as a firefighter and a receiver that is connected to these sensor and transmitter via a network. A single transmitter is connected to a single transfer device in the previous exemplary embodiments. In the third exemplary embodiment, a plurality of transmitters are connected to a single transfer device. Although the number of transfer devices to be worn by the user is reduced, the traffic volume in the transfer devices increases. Even when the traffic volume increases, the following processing is performed in order to suppress the effect on the detection of abnormality in the receiver.

The transfer device sets priority to each of the plurality of transmitters and preferentially transfers detected information from a transmitter with high priority. When a plurality of sensors are worn by a single user, different biological information is measured for each sensor. Biological information includes those whose values change steeply such as cardioelectricity, myoelectricity, pulse wave, and heart rate and also those whose values change slowly such as body temperature. A high priority is set to transmitters connected to sensors that measure the former biological information, and a low priority is set to transmitters connected to sensors that measure the latter biological information.

Figure 10:
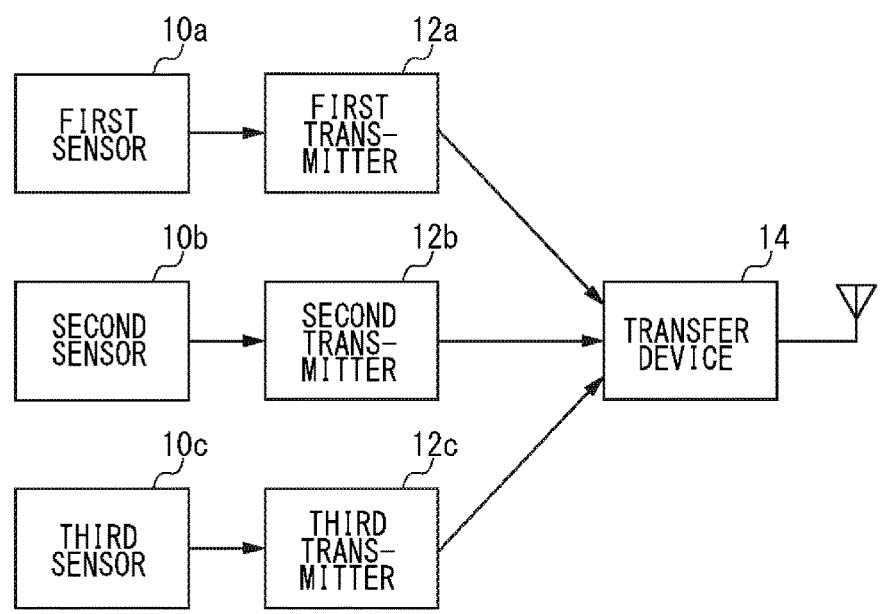
FIG. 10 is a diagram illustrating the configuration of a transmission system according to a third exemplary embodiment.

FIG. 10 illustrates the configuration of a transmission system 150 according to the third exemplary embodiment. The transmission system 150 includes: a first sensor 10a, a second sensor 10b, and a third sensor 10c, which are generically referred to as sensors 10; a first transmitter 12a, a second transmitter 12b, and a third transmitter 12c, which are generically referred to as transmitters 12; and a transfer device 14. The plurality of sensors 10 and the plurality of transmitters 12 are worn by a single user. Each of the sensors 10 measures biological information that is different. A transmitter 12 transmits an information sequence to the transfer device 14 also capable of receiving information sequences from the other transmitters 12. Therefore, the transfer device 14 receives signals that are from the plurality of transmitters 12 and in which information sequences are included.

Upon receiving the signals from the plurality of transmitters 12, the transfer device 14 stores, in a buffer, the information sequences included in the signals. The transfer device 14 transmits the signals that include the information sequences stored in the buffer to the base station device 16. After the transmission of the signals, the transfer device 14 deletes the information sequences stored in the buffer. The transfer device 14 measures the data amount of the buffer. If the data amount of the buffer is a threshold or less, the transfer device 14 transfers the information sequences as described previously. On the other hand, if the data amount of the buffer is larger than the threshold, the transfer device 14 performs the transfer considering the degree of priority. In other words, the transfer device 14 defines priority to each of the plurality of transmitters 12.

Figure 11:
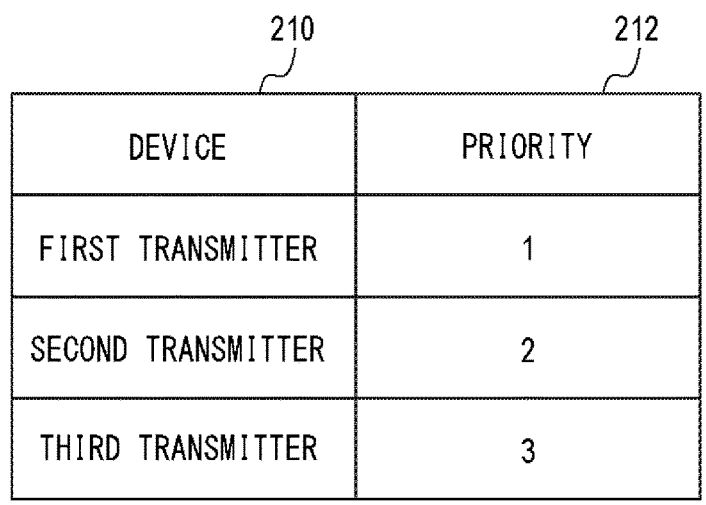
FIG. 11 is a diagram illustrating a data structure of a table stored in a transfer device shown in FIG. 10.

FIG. 11 illustrates a data structure of a table stored in the transfer device 14. As illustrated in the figure, a device column 210 and a priority column 212 are included. Priority is assigned to each of the transmitters 12. The degree of priority "1" is the highest, and the degree of priority "3" is the lowest in this case. This is because the value of biological information measured by the first sensor 10a connected to the first transmitter 12a changes the most rapidly, and the value of biological information measured by the third sensor 10c connected to the third transmitter 12c changes the most moderately. FIG. 10 is referred back. The transfer device 14 preferentially transmits an information sequence from a transmitter 12 with high priority while referring to the table shown in FIG. 11.

Figure 12:
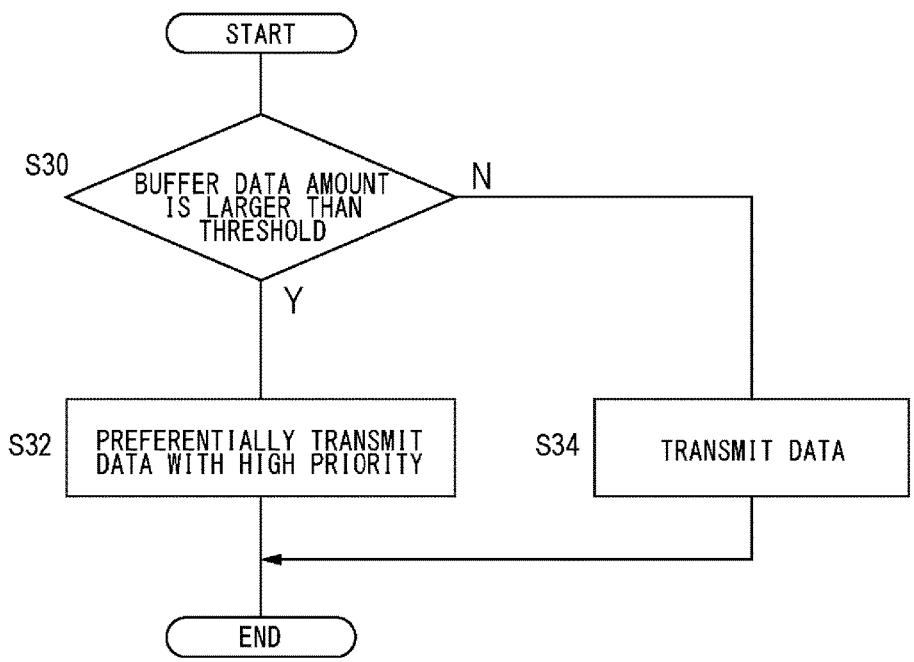
FIG. 12 is a flowchart illustrating a transmission procedure performed by the transfer device shown in FIG. 10.

An explanation will be given of the operation of the transmission system 150 having the above-stated configuration. FIG. 12 is a flowchart illustrating a transmission procedure performed by the transfer device 14. If the data amount of the buffer is larger than the threshold (Y in S30), the transfer device 14 preferentially transmits data with high priority (S32). On the other hand, if the data amount of the buffer is not larger than the threshold (N in S30), the transfer device 14 transmits data (S34).

According to the exemplary embodiment, since a plurality of transmitters are connected to a single transfer device, the number of transfer devices can be reduced. Priority is defined for each of the plurality of transmitters, and an information sequence from a transmitter with high priority is preferentially transmitted. Thus, even when the traffic volume is increased, an increase in transmission delay of an important information sequence can be suppressed. Also, since an increase in transmission delay of an important information sequence is suppressed, the effect on early detection of an abnormal state can be reduced.

Fourth Exemplary Embodiment

A fourth exemplary embodiment will be described next. As in the case of the previous exemplary embodiments, the fourth exemplary embodiment relates to an information analysis system that includes a transmitter worn by a user such as a firefighter and a receiver that is connected to the transmitter via a network. On the other hand, although a sensor is connected to a transmitter in the previous exemplary embodiments, an imaging device is connected to a transmitter in the fourth exemplary embodiment. When a single target object is imaged by two or more imaging devices whose relative position information is known by a GPS, a stereo image is acquired. Thus, one of the purposes of the exemplary embodiment is to identify a hazardous place in detail even when the image is viewed from a remote location by analyzing the image in further detail. Another purpose thereof is to recognize a detailed situation of the target object even when instructions are given from a remote location by viewing the surrounding of the target object by a plurality of imaging devices so that firefighter's risks are reduced. In the fourth exemplary embodiment, when image data is to be transmitted from each of the plurality of transmitters, an information sequence in which image data and time information are multiplexed in a time-dividing manner is transmitted. The receiver synchronizes the timing of image data included in a plurality of information sequences based on time information. An explanation will be given mainly regarding the difference from the previous exemplary embodiments and, particularly, from the first exemplary embodiment.

Figure 13:
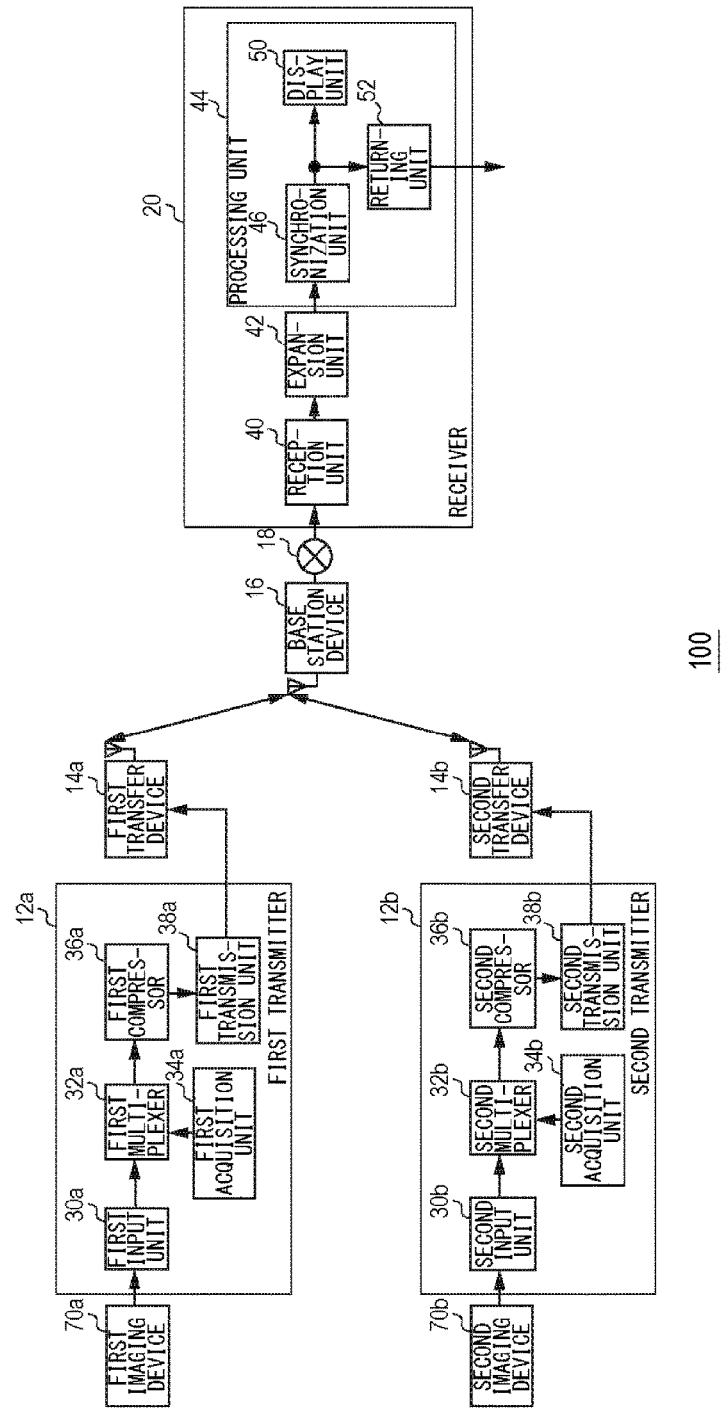
FIG. 13 is a diagram illustrating the configuration of an information analysis system according to a fourth exemplary embodiment.

FIG. 13 illustrates the configuration of an information analysis system 100 according to the fourth exemplary embodiment. The information analysis system 100 includes: a first imaging device 70a and a second imaging device 70b, which are generically referred to as imaging devices 70; a first transmitter 12a and a second transmitter 12b, which are generically referred to as transmitters 12; a first transfer device 14a and a second transfer device 14b, which are generically referred to as transfer devices 14; a base station device 16; a network 18; and a receiver 20. The first transmitter 12a includes: a first input unit 30a; a first multiplexer 32a; a first acquisition unit 34a; a first compressor 36a; and a first transmission unit 38a. The second transmitter 12b includes: a second input unit 30b; a second multiplexer 32b; a second acquisition unit 34b; a second compressor 36b; and a second transmission unit 38b. The first input unit 30a and the second input unit 30b are generically referred to as input units 30. The first multiplexer 32a and the second multiplexer 32b are generically referred to as multiplexers 32. The first acquisition unit 34a and the second acquisition unit 34b are generically referred to as acquisition units 34. The first compressor 36a and the second compressor 36b are generically referred to as compressors 36. The first transmission unit 38a and the second transmission unit 38b are generically referred to as transmission units 38. The receiver 20 includes: a reception unit 40; an expansion unit 42; and a processing unit 44. The processing unit 44 includes: a synchronization unit 46; a display unit 50; and a returning unit 52.

An imaging device 70 images a target object at a scene of disaster and outputs, as image data, an image that is captured. The imaging device 70 is worn, for example, on a firefighter's helmet or the like. The imaging device 70 may use visible light or may use infrared light besides visible light. The latter case allows for night vision and transmission through smoke. The image data is assumed to be a digital value. An input unit 30 inputs image data captured by the imaging device 70.

By inserting time information into the image data that has been input to the input unit 30, a multiplexer 32 generates an information sequence in which the image data and the time information are multiplexed in a time-dividing manner. The reason why the time information is necessary will be explained. By the imaging of a single target object by two imaging devices 70 at the same time, stereo effect is created, and the features of rescue targets and hazardous materials thus become clear. Further, if the baseline length between the imaging devices 70 is found based on position information from a GPS, the distance to the target object can be estimated, and useful information can be obtained for rescue operations performed from a remote location. In the same way as in the first exemplary embodiment, if there is a time difference caused in the reception of image data from the plurality of transmitters 12 due to the base station device 16 and the network 18 that exist along the way, such information can no longer be obtained.

Figure 14:
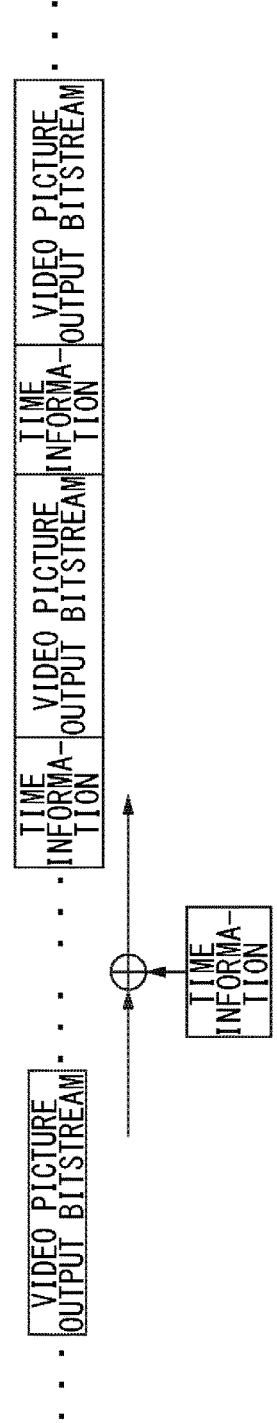
FIG. 14 is a diagram illustrating processing details performed by a multiplexer shown in FIG. 13.

FIG. 14 illustrates processing details performed by the multiplexer 32. Image data from an input unit 30 is shown as "video picture output bitstream." A video picture output bitstream is assumed to include image data for a plurality of images. As shown in the figure, time information is inserted between video picture output bitstreams at predetermined intervals. Image data, which is a single "video picture output bitstream," and a single piece of time information together form a single combination. Such time information in the multiplexer 32 is used to synchronize timing between image data included in an information sequence transmitted from another transmitter 12 and image data in the multiplexer 32. Position information obtained from the GPS may be further inserted. FIG. 13 is referred back.

Based on time information included in each of a plurality of information sequences received by the reception unit 40, the synchronization unit 46 synchronizes timing between respective pieces of image data included in the plurality of information sequences. The same applies to processing performed on the time information for timing synchronization. Thus, the explanation thereof is omitted.

The display unit 50 displays the plurality of pieces of image data whose timing has been synchronized by the synchronization unit 46. For example, a flash of light caused by explosion is confirmed through an image. The display unit 50 may display the image data after performing predetermined analysis on the image data. For example, when the image data is captured by using infrared light, processing for changing colors based on heat is performed. Alternatively, when the plurality of pieces of image data allow for the measurement of distance, processing for multiplexing pieces of distance information is performed. Based on the image data displayed on the display unit 50, a doctor or the like may make a diagnosis. As a result, a judgment is made by a doctor regarding abnormal states. In this case, a commander such as a doctor makes a judgment regarding abnormal states by looking at the image data. Alternatively, an automatic judgment may be made by the receiver 20 or a computer. Further, clouds can be also used. In that case, the automatic judgment is made in a cloud. When abnormality is detected by the diagnosis from the doctor, the returning unit 52 returns the detection result to a predetermined return destination. The return destination may be the user himself/herself, a fire-fighting command vehicle, a family member, or a nearby hospital.

According to the exemplary embodiment, since time information is multiplexed in a time-dividing manner on image data, timing can be synchronized among the pieces of image data. Further, since the timing is synchronized among the pieces of image data, different images captured at the same timing can be displayed. Also, since different images captured at the same timing can be displayed, diagnostic accuracy can be improved. Also, since new time information is generated by the updating of already-acquired time information in the case of a failure in the acquisition of time information based on a signal from a GPS satellite, highly accurate time information can be used. Further, since image data for which infrared light has been used is monitored, a hazardous place can be promptly recognized. Further, since a hazardous place can be promptly recognized, risks that exist before resulting in a loss of life due to suffocation or external injuries can be prevented. Also, a proper judgment is made in a remote control room based on image data so that risks can be avoided and accidents at a scene of disaster can be prevented from occurring.

Fifth Exemplary Embodiment

A fifth exemplary embodiment will be explained next. As in the case of the fourth exemplary embodiment, the fifth exemplary embodiment relates to an information analysis system that includes an imaging device and a transmitter worn by a user such as a firefighter and a receiver that is connected to these imaging device and transmitter via a network. The fifth exemplary embodiment corresponds to a case where the fourth exemplary embodiment and the second exemplary embodiment are combined. The fifth exemplary embodiment as described above is directed to the purpose of updating image data to be processed in the receiver even under a situation where processing delay in the receiver becomes large due to an increase in the traffic volume of a signal received by the receiver. A transmitter according to the fifth exemplary embodiment generates an information sequence by also multiplexing a change tag in a time-dividing manner when multiplexing time information and image data in a time-dividing manner. The change tag represents information that shows the magnitude of a change in the value of the image data. Compression processing and expansion processing are performed in the same way as in the second exemplary embodiment. A description will be made mainly regarding the difference from the previous explanations.

Figure 15:
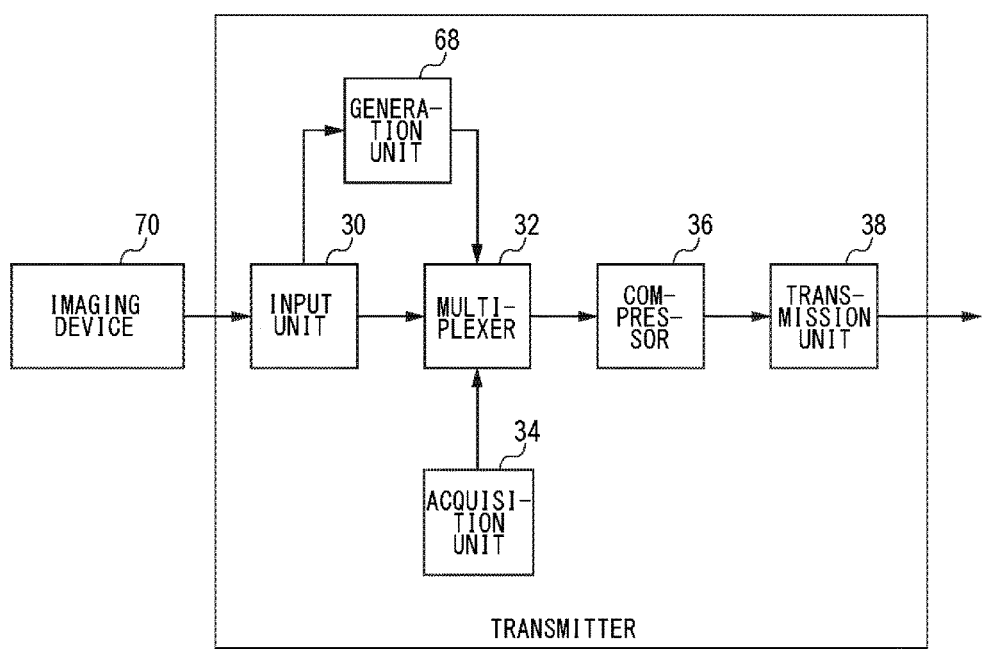
FIG. 15 is a diagram illustrating the configuration of a transmitter according to a fifth embodiment.

FIG. 15 illustrates the configuration of a transmitter 12 according to the fifth exemplary embodiment. The transmitter 12 includes an input unit 30, a multiplexer 32, an acquisition unit 34, a compressor 36, a transmission unit 38, and a generation unit 68. The generation unit 68 derives the magnitude of a change in the value of image data that is input to the input unit 30. The magnitude of the change is derived, for example, as variance and standard deviation in a pixel value among a plurality of images included in image data of the previously-described single combination. The magnitude of the change may be derived as a difference between the maximum value and the minimum value in a pixel value among the plurality of images included in the image data of the single combination. The generation unit 68 generates a change tag based on the magnitude of the change that is derived. The conditions for generating a change tag are the same as those in the second exemplary embodiment. Thus, the explanation thereof is omitted. As described, the generation unit 68 generates a change tag that shows the magnitude of a change in image data that is input to the input unit 30. The generation unit 68 outputs the change tag to the multiplexer 32.

The multiplexer 32 also inputs the change tag from the generation unit 68. The multiplexer 32 also multiplexes, in a time-dividing manner, the change tag generated by the generation unit 68 in addition to image data and time information when generating an information sequence.

The configuration of a receiver 20 in the fifth exemplary embodiment is similar in type to that of FIG. 13. In addition to image data and time information, a change tag that shows the magnitude of a change in the image data is also multiplexed in a time-dividing manner in each of a plurality of information sequences received by a reception unit 40. As described previously, in the information sequences, at least change tags are not subject to compression.

According to the exemplary embodiment, information that can be quickly acquired can be transmitted since change tags are transmitted without being compressed. Also, since change tags are not compressed, processing delay caused until the details of the change tags are checked can be shortened. Since the processing delay caused until the details of the change tags are checked is shortened, the period spent until the checking can be shortened. Also, since time information and image data are checked when a change is shown to be large in change tags, only necessary image data can be acquired in a short period of time.

Sixth Exemplary Embodiment

A sixth exemplary embodiment will be described next. As in the case of the previous exemplary embodiments, the sixth exemplary embodiment relates to an information analysis system that includes a transmitter worn by a user such as a firefighter and a receiver that is connected to the transmitter via a network. In the sixth exemplary embodiment, a sensor is connected to a single transmitter, and an imaging device is connected to another transmitter. Abnormal states are detected by using both biological information and image data. Thus, one of the purposes of the exemplary embodiment is to improve the detection accuracy compared to a case where abnormal states are detected by using either one of biological information and image data.

Figure 16:
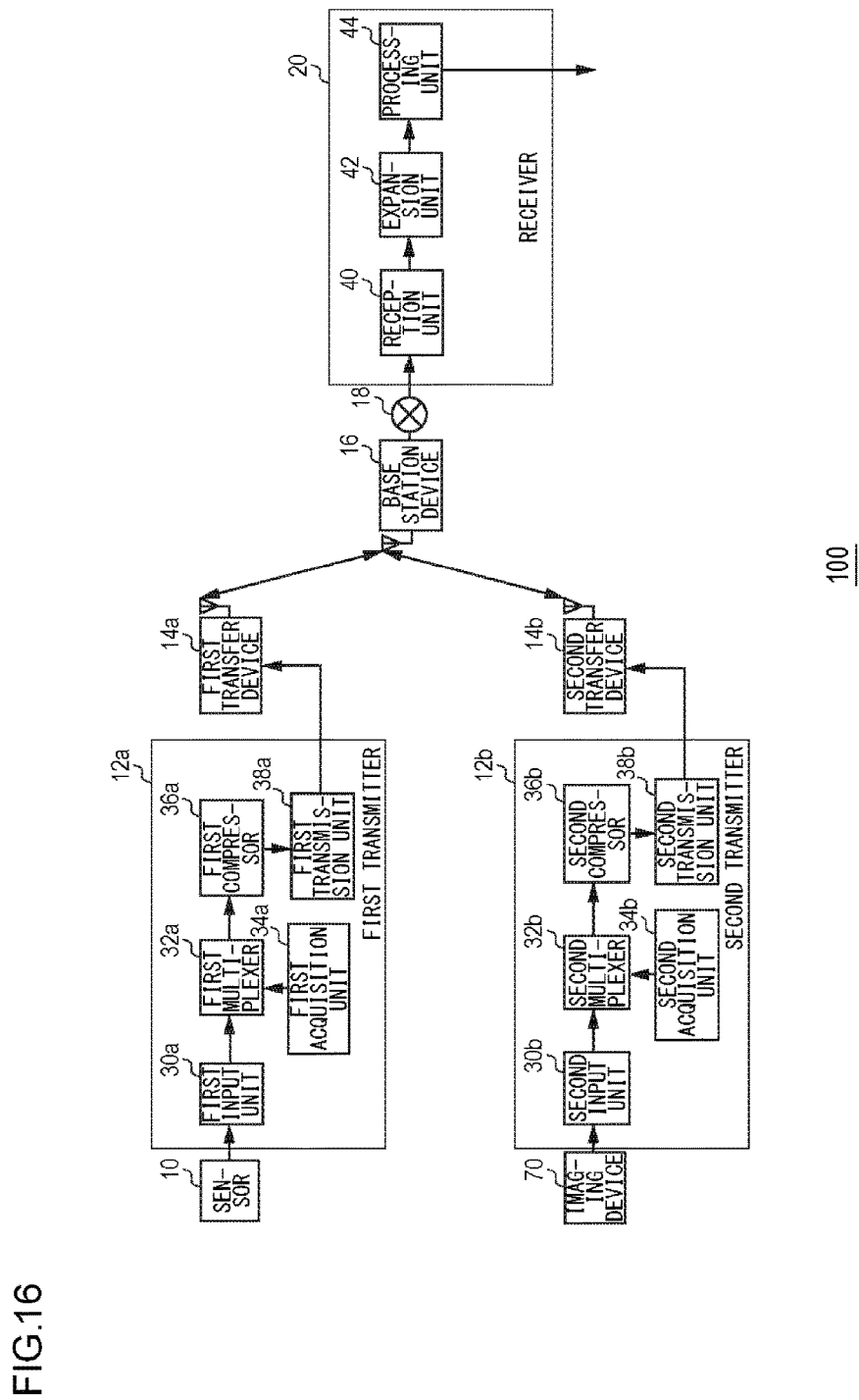
FIG. 16 is a diagram illustrating the configuration of an information analysis system according to a sixth exemplary embodiment.

FIG. 16 is a diagram illustrating the configuration of an information analysis system 100 according to the sixth exemplary embodiment. The information analysis system 100 includes: a sensor 10; an imaging device 70; a first transmitter 12a and a second transmitter 12b, which are generically referred to as transmitters 12; a first transfer device 14a and a second transfer device 14b, which are generically referred to as transfer devices 14; a base station device 16; a network 18; and a receiver 20. The first transmitter 12a includes: a first input unit 30a; a first multiplexer 32a; a first acquisition unit 34a; a first compressor 36a; and a first transmission unit 38a. The second transmitter 12b includes: a second input unit 30b; a second multiplexer 32b; a second acquisition unit 34b; a second compressor 36b; and a second transmission unit 38b. The first input unit 30a and the second input unit 30b are generically referred to as input units 30. The first multiplexer 32a and the second multiplexer 32b are generically referred to as multiplexers 32. The first acquisition unit 34a and the second acquisition unit 34b are generically referred to as acquisition units 34. The first compressor 36a and the second compressor 36b are generically referred to as compressors 36. The first transmission unit 38a and the second transmission unit 38b are generically referred to as transmission units 38. The receiver 20 includes: a reception unit 40; an expansion unit 42; and a processing unit 44. A description will be made mainly regarding the difference from the previous explanations.

The sensor 10, the first transmitter 12a, and the first transfer device 14a are similar in type to corresponding devices shown in the first exemplary embodiment. The imaging device 70, the second transmitter 12b, and the second transfer device 14b are similar in type to corresponding devices shown in the fourth exemplary embodiment.

The first input unit 30a inputs detected information that has been acquired by the sensor 10. The first acquisition unit 34a acquires time information generated based on a signal from a GPS satellite. When the first acquisition unit 34a acquires the time information, the first acquisition unit 34a outputs the time information to the first multiplexer 32a.

When the first acquisition unit 34a fails to acquire the time information, the first acquisition unit 34a outputs time information that is generated by updating already-acquired time information to the first multiplexer 32a. By inserting time information into the detected information that has been input, the first multiplexer 32a generates a first information sequence in which the detected information and the time information are multiplexed in a time-dividing manner. The first compressor 36a compresses the first information sequence and outputs the first information sequence that has been compressed to the first transmission unit 38a. The first transmission unit 38a transmits the compressed first information sequence.

The second input unit 30b inputs image data captured by the imaging device 70. The second acquisition unit 34b acquires time information generated based on a signal from a GPS satellite. When the second acquisition unit 34b acquires the time information, the second acquisition unit 34b outputs the time information to the second multiplexer 32b. When the second acquisition unit 34b fails to acquire the time information, the second acquisition unit 34b outputs time information that is generated by updating already-acquired time information to the second multiplexer 32b. By inserting time information into the image data that has been input, the second multiplexer 32b generates a second information sequence in which the image data and the time information are multiplexed in a time-dividing manner. The second compressor 36b compresses the second information sequence and outputs the second information sequence that has been compressed to the second transmission unit 38b. The second transmission unit 38b transmits the compressed second information sequence. The time information in the first multiplexer 32a and the time information in the second multiplexer 32b are used to synchronize timing between the detected information in the first multiplexer 32a and the image data in the second multiplexer 32b.

The base station device 16, the network 18, and the receiver 20 are similar in type to corresponding devices shown in the first, second, and fourth exemplary embodiments. As well as receiving the first information sequence from the first transmitter 12a, the reception unit 40 receives the second information sequence from the second transmitter 12b. On the first information sequence and the second information sequence that are received by the reception unit 40, compression processing has already been performed. The expansion unit 42 expands the first information sequence and the second information sequence received by the reception unit 40 and outputs the first information sequence and the second information sequence that have been expanded to the processing unit 44. The processing unit 44 processes the first information sequence and the second information sequence received by the reception unit. In particular, based on time information included in the first information sequence and time information includes in the second information sequence, the processing unit 44 synchronizes timing between the detected information included in the first information sequence and the image data included in the second information sequence. Features shown in the second and fifth exemplary embodiments may be added to the information analysis system 100 in the sixth exemplary embodiment.

According to the exemplary embodiment, since the timing is synchronized between detected information and image data, detailed analysis can be performed where biological information and images are used. Also, since detailed analysis where biological information and images are performed, the accuracy of detecting an abnormal state can be improved. Further, by including a change tag, processing delay caused in a receiver can be shortened.

Seventh Exemplary Embodiment

A seventh exemplary embodiment will be explained next. The seventh exemplary embodiment corresponds to a case where the sixth exemplary embodiment and the third exemplary embodiment are combined. In the seventh exemplary embodiment, a plurality of transmitters are connected to a single transfer device, a sensor is connected to any one of the plurality of transmitters, and an imaging device is connected to another transmitter. The transfer device sets priority to each of the plurality of transmitters and preferentially transfers detected information from a transmitter with high priority.

Figure 17:
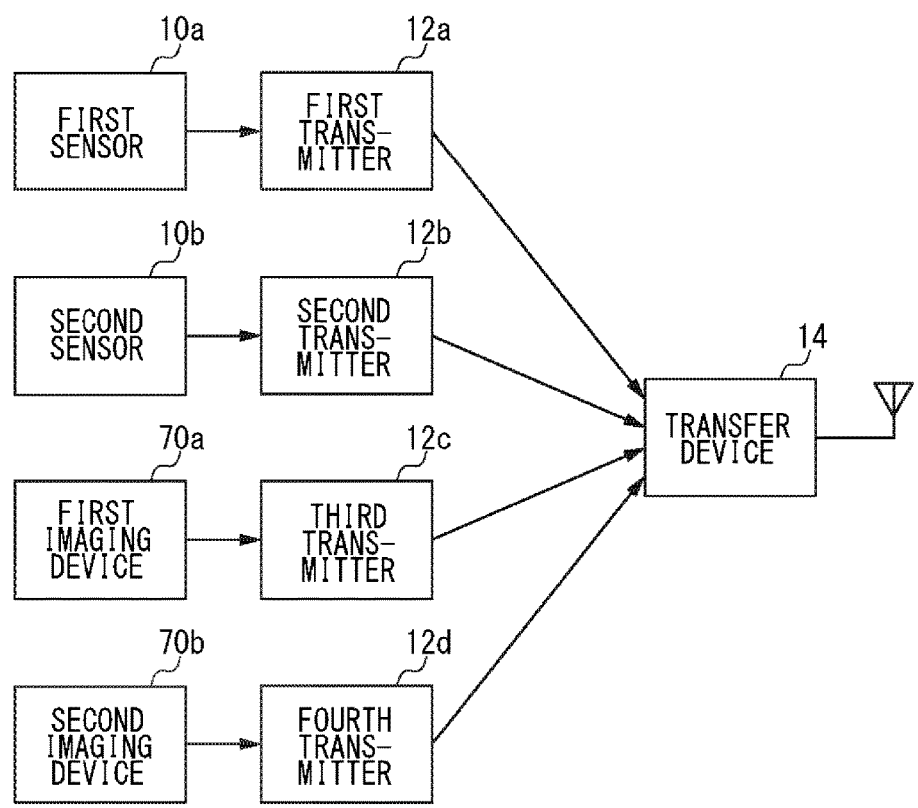
FIG. 17 is a diagram illustrating the configuration of a transmission system according to a seventh embodiment.

FIG. 17 is a diagram illustrating the configuration of a transmission system 150 according to the seventh exemplary embodiment. The transmission system 150 includes: a first sensor 10a and a second sensor 10b, which are generically referred to as sensors 10; a first imaging device 70a and a second imaging device 70b, which are generically referred to as imaging devices 70; a first transmitter 12a, a second transmitter 12b, a third transmitter 12c, and a fourth transmitter 12d, which are generically referred to as transmitters 12; and a transfer device 14. These are worn by a single user. Each of the sensors 10 measures biological information that is different, and each of the imaging devices 70 captures image data that is different. The first transmitter 12a and the second transmitter 12b transmit a first information sequence to the transfer device 14, and the third transmitter 12c and the fourth transmitter 12d transmit a second information sequence to the transfer device 14. As well as receiving the first information sequence from the first transmitter 12a and the second transmitter 12b, the transfer device 14 also receives the second information sequence from the third transmitter 12c and the fourth transmitter 12d.

Upon receiving the signals from the plurality of transmitters 12, the transfer device 14 stores, in a buffer, the information sequences included in the signals. In the same way as in the third exemplary embodiment, if the data amount of the buffer is larger than a threshold, the transfer device 14 preferentially transmits an information sequence with a higher degree of priority in consideration of the degree of priority. For example, the degree of priority for a transmitter 12 connected to the sensor 10 is set to be higher than the degree of priority for a transmitter 12 connected to the imaging device 70.

According to the exemplary embodiment, since a plurality of transmitters are connected to a single transfer device, the number of transfer devices can be reduced. Also, since the degree of priority for a transmitter connected to a sensor is set to be higher than the degree of priority for a transmitter connected to an imaging device, detected information can be preferentially transmitted.

Described above is an explanation based on the exemplary embodiments of the present invention. These exemplary embodiments are intended to be illustrative only, and it will be obvious to those skilled in the art that various modifications to constituting elements and processes could be developed and that such modifications are also within the scope of the present invention.

A multiplexer 32 inserts time information in the first through seventh exemplary embodiments. Alternatively, for example, a multiplexer 32 may change an interval for inserting time information based on the type of detected information that is input to an input unit 30. More specifically, an interval for inserting time information is shortened for detected information with a large change, and an interval for inserting time information is lengthened for detected information with not much change. According to the exemplary embodiment, time information can be efficiently transmitted.

A multiplexer 32 inserts time information in the first through seventh exemplary embodiments. Alternatively, for example, a multiplexer 32 may change an interval for inserting time information based on the type of detected information that is input to an input unit 30. More specifically, an interval for inserting time information is shortened when a change in detected information becomes large, and an interval for inserting time information is lengthened when a change in detected information becomes small. According to the exemplary embodiment, time information can be efficiently transmitted.

A sensor 10 measures biological information in the first through third and exemplary embodiments and in the sixth and seventh exemplary embodiments. Alternatively, for example, a sensor 10 may measure information other than biological information such as temperature, oxygen concentration, the amount of radiation, etc. According to the present exemplary embodiment, temperature, oxygen concentration, and the amount of radiation can be detected from a thermograph image or a temperature sensor, an oxygen concentration sensor, and a radiation dosimeter sensor, respectively.

In the second, fifth, and sixth exemplary embodiments, the value "0" or "1" is assigned to a change tag. Alternatively, for example, a plurality of values may be assigned to a change tag. According to the present exemplary embodiment, whether or not the expansion processing in the receiver 20 is performed can be determined in detail.

The exemplary embodiments may be specified by the following items.

Item 1-1

A transmitter comprising:

an input unit that inputs detected information acquired by a sensor;

a multiplexer that generates an information sequence including the detected information and time information that corresponds to the detected information; and a transmission unit that transmits the information sequence generated by the multiplexer, wherein the time information in the multiplexer is used to synchronize timing between detected information included in an information sequence transmitted from another transmitter and the detected information in the multiplexer.

Item 1-2

The transmitter according to Item 1-1, further comprising:

an acquisition unit that acquires time information generated based on a signal from the outside, wherein, when the acquisition unit acquires the time information, the acquisition unit outputs the time information to the multiplexer, and, when the acquisition unit fails to acquire the time information, the acquisition unit outputs time information that is generated by updating already-acquired time information to the multiplexer.

Item 1-3

The transmitter according to Item 1-1 or Item 1-2, wherein the multiplexer changes an interval for inserting time information based on the type of the detected information that is input to the input unit.

Item 1-4

The transmitter according to any one of Item 1-1 through Item 1-3, wherein the multiplexer changes an interval for inserting the time information based on a change in the value of the detected information that is input to the input unit.

Item 1-5

The transmitter according to any one of Item 1-1 through Item 1-4, further comprising:

a generation unit that generates a change tag that shows the magnitude of a change in the value of the detected information that is input to the input unit; and a compressor that compresses the information sequence generated in the multiplexer and outputs the information sequence that has been compressed to the transmission unit, wherein the multiplexer also multiplexes, in a time-dividing manner, the change tag generated by the generation unit in addition to the detected information and the time information when generating the information sequence, and wherein the compressor excludes, in the information sequence, at least the change tag from being compressed.

Item 1-6

The transmitter according to any one of Item 1-1 through Item 1-5, wherein the transmission unit transmits the information sequence to a transfer device that is also capable of receiving an information sequence from another transmitter, and wherein, in the transfer device, priority is set to each of a plurality of transmitters, and an information sequence from a transmitter with high priority is preferentially transmitted.

Item 1-7

A receiver comprising:

a reception unit that receives an information sequence including detected information and time information that corresponds to the detected information from a plurality of transmitters; and a processing unit that processes, based on time information included in a plurality of information sequences received by the reception unit, detected information included in the plurality of information sequences.

Item 1-8

The receiver according to Item 1-7, further comprising:

an expansion unit that expands the plurality of information sequences received by the reception unit, each on which compression processing has already been performed, and outputs the plurality of information sequences that have been expanded to the processing unit, wherein, in addition to the detected information and the time information, a change tag that shows the magnitude of a change in the value of the detected information is also multiplexed in a time-dividing manner in each of the plurality of information sequences received by the reception unit, and, in the information sequences, at least the change tag is excluded from being compressed, and wherein the expansion unit determines, based on the change tag, whether or not expansion is to be performed.

Item 1-9

An information analysis system comprising: a processing unit that performs time synchronization, among a plurality of information sequences generated to include detected information and time information corresponding to the detected information, based on the time information and analyzes the plurality of information sequences.

Item 1-10

The information analysis system according to Item 1-9, further comprising: an information sequence generation unit that generates the information sequences including the detected information and the time information corresponding to the detected information.

Item 1-11

The information analysis system according to Item 1-10, further comprising:

a sensor that acquires the detected information; and an acquisition unit that acquires the time information based on a signal from the outside.

Item 1-12

An information analysis method comprising: performing time synchronization, among a plurality of information sequences generated to include detected information and time information corresponding to the detected information, based on the time information and analyzing the plurality of information sequences.

Item 1-13

The information analysis method according to Item 1-12, further comprising: generating the information sequences including the detected information and the time information corresponding to the detected information.

Item 1-14

The information analysis method according to Item 1-13, further comprising:

acquiring the detected information from a sensor; and acquiring the time information based on a signal from the outside.

Item 1-15

A transmitter comprising:

an input unit that inputs detected information;

an information sequence generation unit that generates an information sequence including the detected information that has been input to the input unit and time information that corresponds to the detected information; and a transmission unit that transmits the information sequence generated by the information sequence generation unit.

Item 1-16

The transmitter according to Item 1-15, further comprising:

an acquisition unit that acquires the time information based on a signal from the outside, wherein, when the acquisition unit acquires the time information, the acquisition unit outputs the time information to the information sequence generation unit, and, when the acquisition unit fails to acquire the time information, the acquisition unit outputs time information that is generated based on already-acquired time information to the information sequence generation unit.

Item 1-17

An information analysis system comprising:

a plurality of transmitters; and a receiver, wherein each of the plurality of transmitters includes:

an input unit that inputs detected information;

an information sequence generation unit that generates an information sequence including the detected information that has been input to the input unit and time information that corresponds to the detected information; and a transmission unit that transmits the information sequence generated by the information sequence generation unit, and wherein the receiver includes:

a reception unit that receives respective information sequences from the plurality of transmitters; and a processing unit that analyzes, based on time information included in the plurality of information sequences received by the reception unit, detected information included in the plurality of information sequences.

Item 2-1

A transmitter comprising:

an input unit that inputs image data captured by an imaging device;

a multiplexer that generates an information sequence including the image data that has been input to the input unit and time information that corresponds to the image data; and a transmission unit that transmits the information sequence generated by the multiplexer, wherein the time information in the multiplexer is used to synchronize timing between image data included in an information sequence transmitted from another transmitter and the image data in the multiplexer.

Item 2-2

The transmitter according to Item 2-1, further comprising:

a generation unit that generates a change tag that shows the magnitude of a change in the image data that is input to the input unit; and a compressor that compresses the information sequence generated in the multiplexer and outputs the information sequence that has been compressed to the transmission unit, wherein the multiplexer also multiplexes, in a time-dividing manner, the change tag generated by the generation unit in addition to the image data and the time information when generating the information sequence, and wherein the compressor excludes, in the information sequence, at least the change tag from being compressed.

Item 2-3

The transmitter according to Item 2-1 or 2-2, further comprising:

an acquisition unit that acquires time information generated based on a signal from the outside;

wherein, when the acquisition unit acquires the time information, the acquisition unit outputs the time information to the multiplexer, and, when the acquisition unit fails to acquire the time information, the acquisition unit outputs time information that is generated by updating already-acquired time information to the multiplexer.

Item 2-4

A receiver comprising:

a reception unit that receives an information sequence including image data and time information that corresponds to the image data from a plurality of transmitters; and a processing unit that processes, based on time information included in a plurality of information sequences received by the reception unit, image data included in the plurality of information sequences.

Item 2-5

The receiver according to Item 2-4, further comprising:

an expansion unit that expands the plurality of information sequences received by the reception unit, each on which compression processing has already been performed, and outputs the plurality of information sequences that have been expanded to the processing unit, wherein, in addition to the image data and the time information, a change tag that shows the magnitude of a change in the image data is also multiplexed in a time-dividing manner in each of the plurality of information sequences received by the reception unit, and, in the information sequences, at least the change tag is excluded from being compressed, and wherein the expansion unit determines, based on the change tag, whether or not expansion is to be performed.

Item 2-6

An information analysis system comprising: a processing unit that performs time synchronization, among a plurality of information sequences generated to include image data and time information corresponding to the image data, based on the time information and analyzes the plurality of information sequences.

Item 2-7

The information analysis system according to Item 2-6, further comprising: an information sequence generation unit that generates the information sequences including the image data and the time information corresponding to the image data.

Item 2-8

The information analysis system according to Item 2-7, further comprising:
an imaging device that acquires the image data; and
an acquisition unit that acquires the time information based on a signal from the outside.

Item 2-9

An information analysis method comprising: performing time synchronization, among a plurality of information sequences generated to include image data and time information corresponding to the image data, based on the time information and analyzing the plurality of information sequences.

Item 2-10

The information analysis method according to Item 2-9, further comprising: generating the information sequences including the image data and the time information corresponding to the image data.

Item 2-11

The information analysis method according to Item 2-10, further comprising:
acquiring the image data from the imaging device; and
acquiring the time information based on a signal from the outside.

Item 2-12

A transmitter comprising:
an input unit that inputs image data;
an information sequence generation unit that generates an information sequence including the image data that has been input to the input unit and time information that corresponds to the image data; and
a transmission unit that transmits the information sequence generated by the information sequence generation unit.

Item 2-13

The transmitter according to Item 2-12, further comprising:
an acquisition unit that acquires the time information based on a signal from the outside;
wherein, when the acquisition unit acquires the time information, the acquisition unit outputs the time information to the information sequence generation unit, and, when the acquisition unit fails to acquire the time information, the acquisition unit outputs time information that is generated based on already-acquired time information to the information sequence generation unit.

Item 2-14

An information analysis system comprising:
a plurality of transmitters; and
a receiver,
wherein each of the plurality of transmitters includes:
an input unit that inputs image data;
an information sequence generation unit that generates an information sequence including the image data that has been input to the input unit and time information that corresponds to the image data; and
a transmission unit that transmits the information sequence generated by the information sequence generation unit,
wherein the receiver includes:
a reception unit that receives respective information sequences from the plurality of transmitters; and
a processing unit that analyzes, based on time information included in the plurality of information sequences received by the reception unit, image data included in the plurality of information sequences.

Item 3-1

A transmission system comprising:
a first transmitter that transmits a first information sequence including detected information acquired by a sensor and time information that corresponds to the detected information;
a second transmitter that transmits a second information sequence including image data captured by an imaging device and time information that corresponds to the image data,
wherein the time information in the first information sequence and the time information in the second information sequence are used to synchronize timing between the detected information and the image data.

Item 3-2

The transmission system according to Item 3-1,
wherein the first transmitter further includes:
a first acquisition unit that acquires time information generated based on a signal from the outside; and
a first multiplexer that generates, by inserting the time information into the detected information that has been input, a first information sequence in which the detected information and the time information are multiplexed in a time-dividing manner,
wherein, when the first acquisition unit acquires the time information, the first acquisition unit outputs the time information to the first multiplexer, and, when the first acquisition unit fails to acquire the time information, the first acquisition unit outputs time information that is generated by updating already-acquired time information to the first multiplexer,
wherein the second transmitter further includes:
a second acquisition unit that acquires time information generated based on a signal from the outside; and
a second multiplexer that generates, by inserting the time information into the image data that has been input, a second information sequence in which the image data and the time information are multiplexed in a time-dividing manner, and
wherein, when the second acquisition unit acquires the time information, the second acquisition unit outputs the time information to the second multiplexer, and, when the second acquisition unit fails to acquire the time information, the second acquisition unit outputs time information that is generated by updating already-acquired time information to the second multiplexer.

Item 3-3

The transmission system according to Item 3-2, wherein the first multiplexer changes an interval for inserting the time information based on the type of the detected information that is input.

Item 3-4

The transmission system according to Item 3-2 or 3-3, wherein the first multiplexer changes an interval for inserting the time information based on a change in the value of the detected information that is input.

Item 3-5

The transmission system according to any one of Item 3-2 through Item 3-4, wherein the first transmitter further includes:

a first generation unit that generates a change tag that shows the magnitude of a change in the value of the detected information that is input; and a first compressor that compresses the first information sequence generated by the first multiplexer, wherein the first multiplexer also multiplexes, in a time-dividing manner, the change tag generated by the first generation unit in addition to the detected information and the time information when generating the first information sequence, wherein the first compressor excludes, in the first information sequence, at least the change tag from being compressed, wherein the second transmitter further includes:

a second generation unit that generates a change tag that shows the magnitude of a change in the image data that is input;

a second compressor that compresses the second information sequence generated by the second multiplexer, wherein the second multiplexer also multiplexes, in a time-dividing manner, the change tag generated by the second generation unit in addition to the image data and the time information when generating the second information sequence, and wherein the second compressor excludes, in the second information sequence, at least the change tag from being compressed.

Item 3-6

The transmission system according to any one of Item 3-1 through Item 3-5, further comprising:

a transfer device that also receives the second information sequence from the second transmitter as well as receiving the first information sequence from the first transmitter, wherein the transfer device sets priority to each of the first transmitter and the second transmitter and preferentially transmits the information sequences in the descending order of priority.

Item 3-7

A receiver comprising:

a reception unit that receives, as well as receiving a first information sequence including detected information and time information that corresponds to the detected information from a first transmitter, a second information sequence including image data and time information that corresponds to the image data from a second transmitter; and a processing unit that processes, based on time information included in the first and second information sequences received by the reception unit, at least either the detected information or the image data included in the first information sequence or the second information sequence.

Item 3-8

The receiver according to Item 3-7, further comprising:

an expansion unit that expands the first and second information sequences received by the reception unit, on which compression processing has already been performed, and outputs the first and second information sequences that have been expanded to the processing unit, wherein, in addition to the detected information and the time information, a change tag that shows the magnitude of a change in the value of the detected information is also multiplexed in a time-dividing manner in the first information sequence received by the reception unit, and, in the first information sequence, at least the change tag is excluded from being compressed, wherein, in addition to the image data and the time information, a change tag that shows the magnitude of a change in the image data is also multiplexed in a time-dividing manner in the second information sequence received by the reception unit, and, in the second information sequence, at least the change tag is excluded from being compressed, and wherein the expansion unit determines, based on the change tags, whether or not expansion is to be performed.

Item 3-9

An information analysis system that performs synchronization, between a first information sequence generated to include detected information and time information corresponding to the detected information and a second information sequence generated to include image data and time information corresponding to the image data, based on the respective pieces of time information and analyzes the first information sequence and the second information sequence.

Item 3-10

The information analysis system according to Item 3-9, further comprising:

a first information sequence generation unit that generates the first information sequence including the detected information and the time information that corresponds to the detected information; and a second information sequence generation unit that generates the second information sequences including the image data and the time information corresponding to the image data.

Item 3-11

The information analysis system according to Item 3-10, further comprising:

a sensor that acquires the detected information;

an imaging device that acquires the image data; and an acquisition unit that acquires the pieces of time information based on an external signal.

Item 3-12

An information analysis method for performing synchronization, between a first information sequence generated to include detected information and time information corresponding to the detected information and a second information sequence generated to include image data and time information corresponding to the image data, based on the respective pieces of time information and analyzing the first information sequence and the second information sequence.

Item 3-13

The information analysis method according to Item 3-12, further comprising:

generating the first information sequence including the detected information and the time information that corresponds to the detected information; and generating the second information sequence including the image data and the time information corresponding to the image data.

Item 3-14

The information analysis method according to Item 3-13, further comprising:

acquiring the detected information from a sensor;

acquiring the image data from an imaging device; and acquiring the pieces of time information based on an external signal.

Item 3-15

A transmission system comprising a first transmitter and a second transmitter, wherein the first transmitter includes:

a first input unit that inputs detected information;

a first information sequence generation unit that generates a first information sequence including the detected information that has been input to the first input unit and time information that corresponds to the detected information; and a first transmission unit that transmits the first information sequence generated by the first information sequence generation unit, and wherein the second transmitter includes:

a second input unit that inputs image data;

a second information sequence generation unit that generates a second information sequence including the image data that has been input to the second input unit and time information that corresponds to the image data; and a transmission unit that transmits the second information sequence generated by the second information sequence generation unit.

Item 3-16

The transmission system according to Item 3-15, wherein the first transmitter further includes:

a first acquisition unit that acquires time information based on a signal from the outside;

wherein, when the first acquisition unit acquires the time information, the first acquisition unit outputs the time information to the first information sequence generation unit, and, when the first acquisition unit fails to acquire the time information, the first acquisition unit outputs time information that is generated based on already-acquired time information to the first information sequence generation unit, wherein the second transmitter further includes:

a second acquisition unit that acquires time information based on a signal from the outside; and wherein, when the second acquisition unit acquires the time information, the second acquisition unit outputs the time information to the second information sequence generation unit, and, when the second acquisition unit fails to acquire the time information, the second acquisition unit outputs time information that is generated based on already-acquired time information to the second information sequence generation unit.

Item 3-17

An information analysis system comprising:

a first transmitter and a second transmitter; and a receiver, wherein the first transmitter includes:

a first input unit that inputs detected information; a first information sequence generation unit that generates a first information sequence including the detected information that has been input to the first input unit and time information that corresponds to the detected information; and a first transmission unit that transmits the first information sequence generated by the first information sequence generation unit, wherein the second transmitter includes:

a second input unit that inputs image data;

a second information sequence generation unit that generates a second information sequence including the image data that has been input to the second input unit and time information that corresponds to the image data; and a first transmission unit that transmits the second information sequence generated by the second information sequence generation unit, and wherein the receiver includes:

a reception unit that receives the first information sequence and the second information sequence from the first transmitter and the second transmitter, respectively; and a processing unit that analyzes, based on the respective pieces of time information included in the first and second information sequences received by the reception unit, the detected information or the image data included in the first information sequence or the second information sequence.

What is claimed is:

1. An information analysis system comprising:
a plurality of transmitters; and
a receiver;
wherein each of the plurality of transmitters includes:
an inputting processor that inputs detected information,
a multiplexor that generates an information sequence including the detected information that has been input to the inputting processor and time information that corresponds to the detected information,
a transmitting processor that transmits the information sequence generated by the multiplexor, and
an acquiring processor that acquires time information generated based on a signal from the outside,
wherein, when the acquiring processor acquires the time information, the acquiring processor outputs the time information to the multiplexor,
and, when the acquiring processor fails to acquire the time information, the acquiring processor outputs time information that is generated by updating already-acquired time information to the multiplexor,
wherein the receiver includes:
receiving processor that receives respective information sequences from the plurality of transmitters, and
a processor that analyzes, based on time information included in the plurality of information sequences received by the receiving processor, detected information included in the plurality of information sequences,
wherein each of the plurality of transmitters further includes an imaging device, and
wherein the detected information is image data imaged by the imaging device.

2. An information analysis system comprising:
a plurality of transmitters; and
a receiver;
wherein each of the plurality of transmitters includes:
an inputting processor that inputs detected information,
a multiplexor that generates an information sequence including the detected information that has been input to the inputting processor and time information that corresponds to the detected information,
a transmitting processor that transmits the information sequence generated by the multiplexor,
a generating processor that generates a change tag that shows the magnitude of a change in the value of the detected information that is input to the processor,
a compressor that compresses the information sequence generated in the multiplexor and outputs the information sequence that has been compressed to the transmitting processor,
wherein the multiplexor also multiplexes, in a time-dividing manner, the change tag generated by the generating processor in addition to the detected information and the time information when generating the information sequence, and
wherein the compressor excludes, in the information sequence, at least the change tag from being compressed,
wherein the receiver includes:
a receiving processor that receives respective information sequences from the plurality of transmitters, and
a processor that analyzes, based on time information included in the plurality of information sequences received by the receiving processor, detected information included in the plurality of information sequences, wherein each of the plurality of transmitters further includes an imaging device, and wherein the detected information is image data imaged by the imaging device.

3. The information analysis system according to claim 2, wherein the multiplexor changes an interval for inserting time information based on the type of the detected information that is input to the processor.

4. The information analysis system according to claim 2, wherein the multiplexor changes an interval for inserting time information based on a change in the value of the detected information that is input to the processor.

5. An information analysis system comprising:
a plurality of transmitters; and
a receiver;
wherein each of the plurality of transmitters includes:
an inputting processor that inputs detected information,
a multiplexor that generates an information sequence including the detected information that has been input to the inputting processor and time information that corresponds to the detected information, and
a transmitting processor that:
transmits the information sequence generated by the multiplexor to a transfer device that is also capable of receiving an information sequence from another transmitter, and
wherein, in the transfer device, priority is set to each of the plurality of transmitters, and an information sequence from a transmitter with high priority is referentially transmitted,
wherein the receiver includes:
a receiving processor that receives respective information sequences from the plurality of transmitters, and
a processor that analyzes, based on time information included in the plurality of information sequences received by the receiving processor, detected information included in the plurality of information sequences,
wherein each of the plurality of transmitters further includes an imaging device, and
wherein the detected information is image data imaged by the imaging device.

* * * * *